(12) United States Patent
Majeed et al.

(10) Patent No.: US 10,479,749 B2
(45) Date of Patent: Nov. 19, 2019

(54) **PROCESS FOR THE PREPARATION OF STANDARDIZED COMPOSITION OF ARJUNOGLUCOSIDE FROM THE BARK OF *TERMINALIA ARJUNA***

(71) Applicants: Muhammed Majeed, Edison, NJ (US); Kalyanam Nagabhushanam, East Windsor, NJ (US); Beena Bhat, Bangalore (IN)

(72) Inventors: Muhammed Majeed, Edison, NJ (US); Kalyanam Nagabhushanam, East Windsor, NJ (US); Beena Bhat, Bangalore (IN)

(73) Assignee: SAMI LABS LIMITED, Bangalore (IN)

( * ) Notice: Subject to any disclaimer, the term of this patent is extended or adjusted under 35 U.S.C. 154(b) by 0 days.

(21) Appl. No.: 16/014,401

(22) Filed: Jun. 21, 2018

(65) Prior Publication Data
US 2018/0370885 A1    Dec. 27, 2018

Related U.S. Application Data

(60) Provisional application No. 62/522,801, filed on Jun. 21, 2017.

(51) Int. Cl.
| | | |
|---|---|---|
| *C07C 35/44* | (2006.01) | |
| *C07D 311/60* | (2006.01) | |
| *C07H 15/24* | (2006.01) | |
| *A61P 31/12* | (2006.01) | |
| *A61P 35/00* | (2006.01) | |
| *A61K 36/61* | (2006.01) | |

(52) U.S. Cl.
CPC ............ *C07C 35/44* (2013.01); *C07D 311/60* (2013.01); *C07H 15/24* (2013.01); *A61K 36/61* (2013.01); *A61P 31/12* (2018.01); *A61P 35/00* (2018.01); *C07C 2603/52* (2017.05)

(58) Field of Classification Search
CPC ....... C07C 35/44; C07C 62/06; A61K 36/185; A61K 2236/00; A61K 36/61; C07H 15/24; C07D 311/60
See application file for complete search history.

(56) References Cited

PUBLICATIONS

Honda et al, Bulletin of the Chemical Society of Japan, Arjungenin, Arjunglycoside I and Arjunglycoside II. A New Triterpene and New Triterpene Glucosides from Terminalia arjuna, 1976, 49(11), pp. 3213-3218. (Year: 1976).*

Tsujimura, Journal of the Agricultural Chemical Society of Japan, On Tea Catechin Isolated from Green Tea, 1930, 6:6-9, pp. 62-69. (Year: 1930).*

Wahnschafft et al (Industrial & Chemical Industry Research, A Problem Decomposition Approach for the Synthesis of Complex Separation Processes with Recycles, 1993, 32, pp. 1121-1141. (Year: 1993).*

Honda et al., Arjungenin, Arjunglucoside I, and Arjunglucoside II. A New Triterpene and New Triterpene Glucosides from Terminalia arjuna. Bulletin of the Chemical Society of Japan, 1976;49(11):3213-3218.

Tsuyuki et al., A new triterpene compound from Terminalia arjuna. Arjunoglucoside III. Bulletin of the chemical society of Japan, 1979; 52(10); 3127-3128.

Sandhu et al., Effects of Withania somnifera (Ashwagandha) and Terminalia arjuna (Arjuna) on physical performance and cardiorespiratory endurance in healthy young adults, Int J Ayurveda Res, 2010;1(3): 144149.

Pertuit et al., A New Aromatic Compound from the Stem Bark of Terminalia catappa, Nat Prod Commun. 2015;10 (6):1005-1007.

Zafar et al., Terminalia arjuna: Alternative Treatment for Cardiovascular Diseases, Int. J. Pharm. Sci. Rev. Res., 2015;35(2): 52-56.

Patel et al., Development and Validation of Stability Indicating Assay for Arjuna Caplets and Stability Studies with Concurrent Phytochemical Investigations, Inventi Rapid: Planta Activa, 2015;1:1-5.

Chandra Sekhar et al., Terminalia arjuna bark extract attenuates picrotoxin-induced behavioral changes by activation of serotonergic, dopaminergic, GABAergic and antioxidant systems, Chinese Journal of Natural Medicines, 2017, 15 (8): 584-596.

Pawar & Bhutani, Effect of oleanane triterpenoids from Terminalia arjuna—a cardioprotective drug on the process of respiratory oxyburst, Phytomedicine, 2005;25:391-393.

Saxena et al., Cytotoxic agents from Terminalia arjuna, Planta Med. 2007;73(14):1486-90.

A. Anbalagan, Phytochemical and pharmacological studies on Terminalia arjuna (Roxb.) weight & Arnot and Borreria Hispida (Linn.) K. Schum, Ph. D Thesis, http://shodhganga/inflibnet.ac.in/bitstream/10603/4547/8/08_chapter%202.pdf.

\* cited by examiner

*Primary Examiner* — Paul A Zucker

(57) ABSTRACT

Disclosed is a novel process for the isolation of bioactive compounds from *Terminalia arjuna*. More specifically, the invention discloses a process for isolation and enrichment of bioactive compounds Arjunic acid, Arjunolic acid, Arjungenin, Arjunetin, Arjunoglucoside-I, Arjunoglucoside-II, and Catechin from the bark of *Terminalia arjuna*. The invention also discloses a composition standardized to contain 3% arjunoglucosides isolated from the bark of *Terminalia arjuna*.

3 Claims, 16 Drawing Sheets

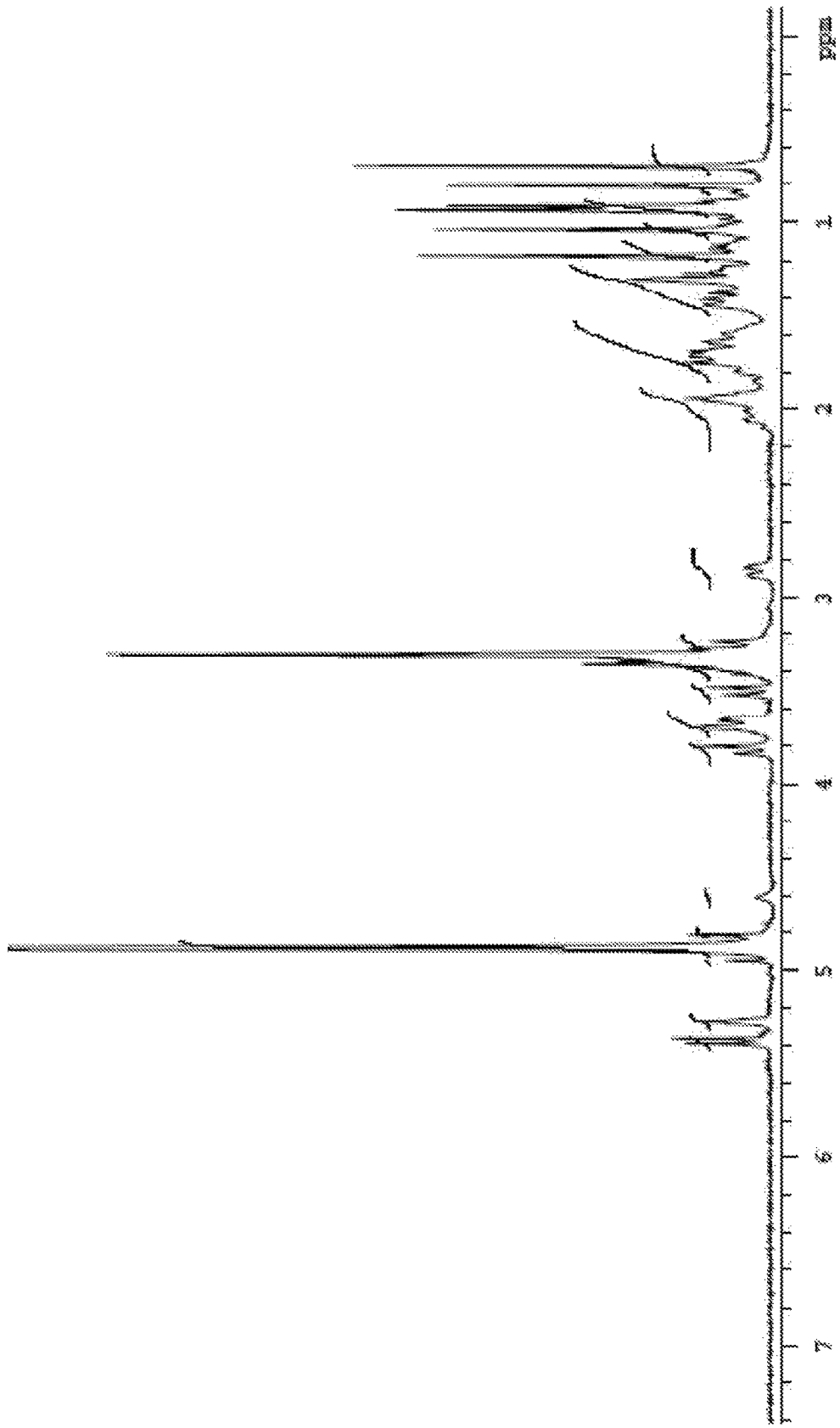

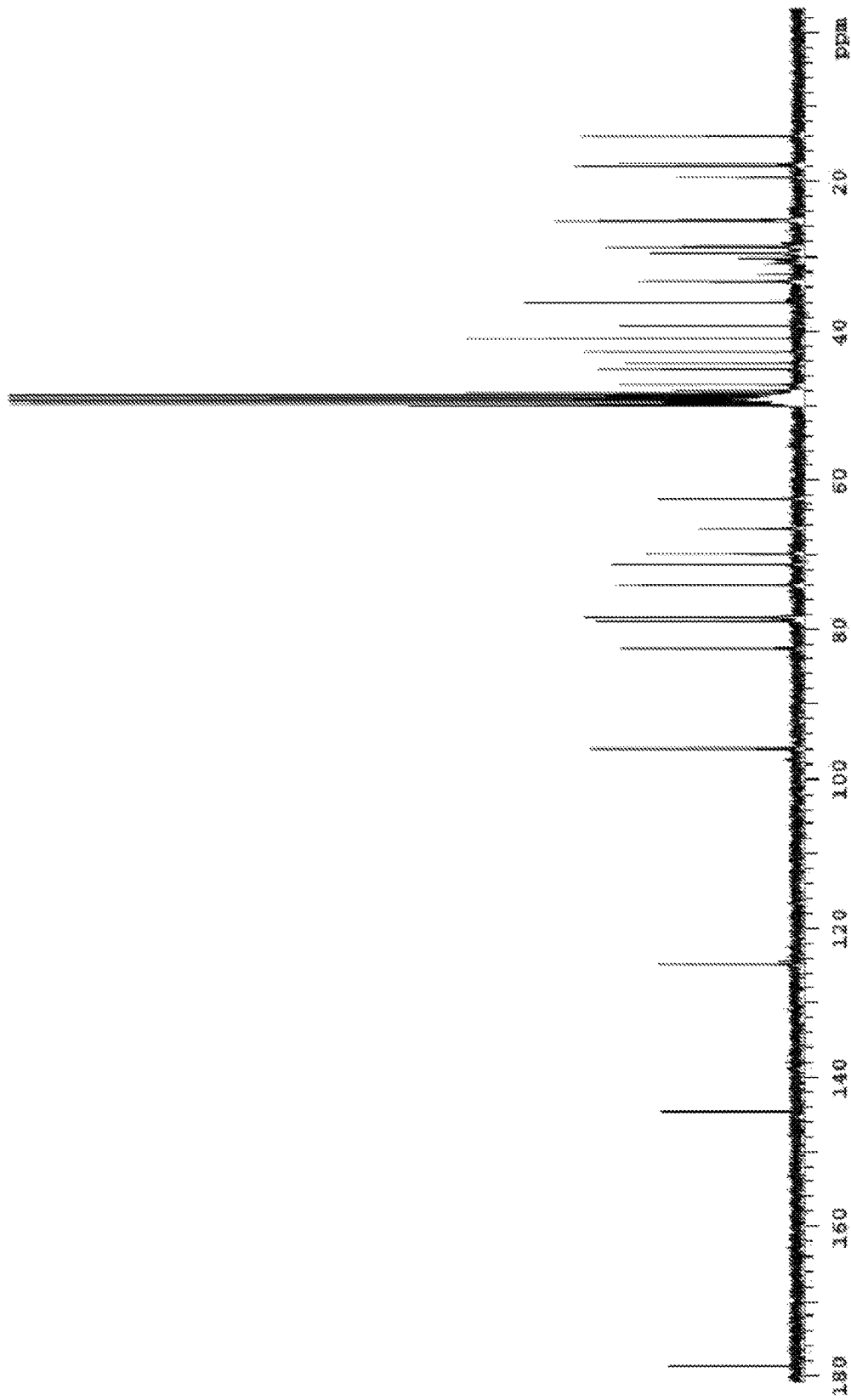

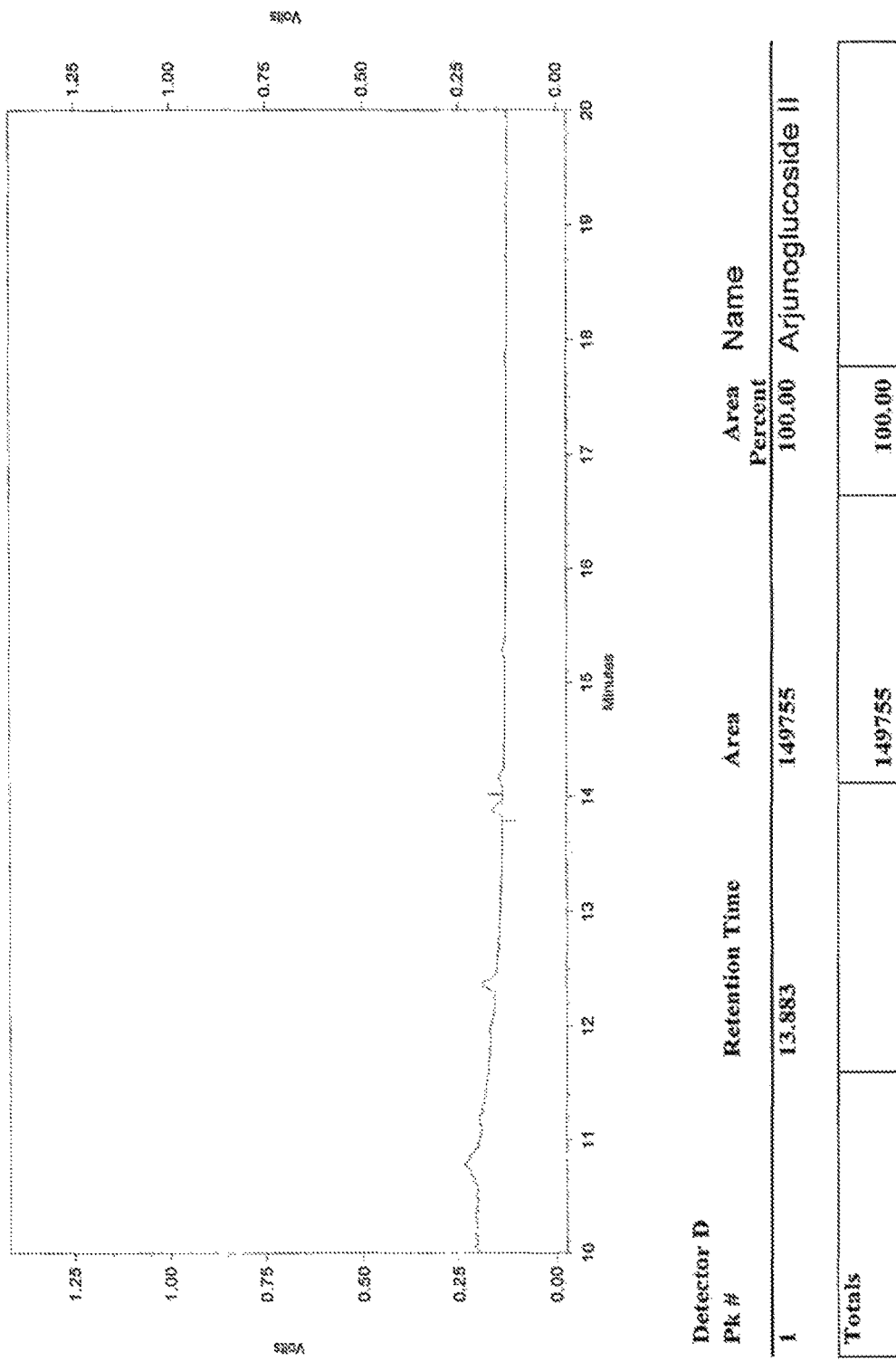

PROCESS FOR THE PREPARATION OF STANDARDIZED COMPOSITION OF ARJUNOGLUCOSIDE FROM THE BARK OF TERMINALIA ARJUNA

CROSS-REFERENCE TO RELATED APPLICATIONS

This is a non-provisional application claiming priority of U.S. provisional applications No. 62/522,801, filed on 21 Jun. 2017.

BACKGROUND OF THE INVENTION

Field of the Invention

The present invention in general relates to bioactive compounds from *Terminalia arjuna*. More specifically the present invention discloses a novel process for the preparation of standardized composition of arjunoglucoside from bark of *Terminalia arjuna*. The standardized composition disclosed in the present invention includes hitherto undisclosed molecules that contribute to the biological effects of said composition.

Description of Prior Art

*Terminalia arjuna* or *arjuna* is a well known medicinal plant used in the ancient Ayurvedic medicine. The bark of *Terminalia arjuna* reported to contain many bioactive compounds, which can be tapped for use in the treatment of many diseases. The following prior art describe the important biological effects of *Terminalia arjuna*.
1. Pawar & Bhutani, Effect of oleanane triterpenoids from *Terminalia arjuna*—a cardioprotective drug on the process of respiratory oxyburst, Phytomedicine, 2005; 25:391-393
2. Sandhu et al., Effects of *Withania somnifera* (Ashwagandha) and *Terminalia arjuna* (*Arjuna*) on physical performance and cardiorespiratory endurance in healthy young adults, Int J Ayurveda Res, 2010; 1(3): 144-149.
3. Zafar et al., *Terminalia arjuna*: Alternative Treatment for Cardiovascular Diseases, Int. J. Pharos. Sci. Rev. Res., 2015; 35(2): 52-56.
4. Patel et al., Development and Validation of Stability Indicating Assay for *Arjuna* Caplets and Stability Studies with Concurrent Phytochemical Investigations, Inventi Rapid: Planta Activa, 2015; 1:1-5.
5. Chandra Sekhar et al., *Terminalia arjuna* bark extract attenuates picrotoxin-induced behavioral changes by activation of serotonergic, dopaminergic, GABAergic and antioxidant systems, Chinese Journal of Natural Medicines, 2017, 15(8): 584-596

Arjunoglucoside, a compound obtained from bark of *Terminalia arjuna* is well documented in literatures for its cardio-protective activity. Other than its cardioprotective property, *Terminalia arjuna* and its bark extract reported for wide range of activities such as anticancer, hepatoprotective, antiviral, antioxidant, anti-asthmatic, anti-fertility, anti-diabetic, wound healing, anti-platelet and anticoagulant, antibacterial and anti-fungal activity. (Saxena et al., Cytotoxic agents from *Terminalia arjuna*, Planta Med. 2007; 73(14): 1486-90).

There are many processes disclosed in the literature for the isolation of Arjunoglucoside and its derivatives from bark of *Terminalia arjuna* and other species of *Terminalia*. Anbalangan et al. (A. Anbalagan, Phytochemical and pharmacological studies on *Terminalia arjuna* (Roxb.) weight & Arnot and Borreria Hispida (Linn.) K. Schum, Ph. D Thesis, http://shodhganga.inflibnet.ac.inibitstream/10603/4547/8/08_chapter%202.pdf (Accessed on 13 Jun. 2018) reported a methanolic extract of stem bark of *Terminalia arjuna* chromatographed over silica gel benzene and eluted with solvents of increasing polarity viz., benzene, chloroform and methanol. Total 6 compounds were identified from methanolic extract of stem bark of *Terminalia arjuna* such as 3-oxo-olean-12-ene-28-oic acid, Methyl maslinate, Hederagenin Methyl ester, Hederagenin, Maslinic acid and Arjunolic acid. The other processes for the isolation of arjunoglucosides are described in the following prior art documents:
1. Tsuyuki et al., A new triterpene compound from *Terminalia arjuna*. Arjunoglucoside III. Bulletin of the chemical society of Japan, 1979; 52(10); 3127-3128
2. Honda et al., Arjungenin, Arjunglucoside I, and Arjunglucoside II. A New Triterpene and New Triterpene Glucosides from *Terminalia arjuna*. Bulletin of the Chemical Society of Japan, 1976; 49(11):3213-3218.
3. Pertuit et al., A New Aromatic Compound from the Stem Bark of *Terminalia catappa*, Nat Prod Commun. 2015; 10(6):1005-1007.

Though the isolation of arjunoglucoside and its derivatives are already reported in the literature, inventors first time reported novel process for the preparation of standardized composition of arjunoglucoside from bark of *Terminalia arjuna*. The novel process for isolation arjunoglucoside and its derivatives is both economically viable and industrially scalable.

The principle objective of the invention is to disclose a novel process for the isolation and preparation of standardized composition of arjunoglucoside from bark of *Terminalia arjuna*.

It is another objective of invention to disclose the novel process for isolation and enrichment of arjunoglucosides.

It is another objective of invention to disclose a composition standardized to contain arjunoglucosides.

The present invention fulfils the aforesaid objectives and provides further related advantages.

SUMMARY OF THE INVENTION

The present invention pertains to a novel process for the isolation of bioactive compounds from *Terminalia arjuna*. More specifically, the invention discloses a process for isolation and enrichment of bioactive compounds Arjunic acid, Arjunolic acid, Arjungenin, Arjunetin, Arjunoglucoside-I, Arjunoglucoside-II, Catechin and Gallocatechin from the bark of *Terminalia arjuna*. The invention also discloses a composition standardized to contain 3% arjunoglucosides isolated from the bark of *Terminalia arjuna*.

BRIEF DESCRIPTION OF THE DRAWINGS

FIG. 1a shows the proton NMR spectrum for the identification of Arjunic acid isolated from the bark of *Terminalia arjuna*.

FIG. 4b shows the carbon NMR spectrum for the identification of Arjunoglucoside-I isolated from the bark of *Terminalia arjuna*.

FIG. 6a shows the HPLC chromotogram for the identification of Arjunoglucoside-II methanolic extract isolated from the bark of *Terminalia arjuna*.

DESCRIPTION OF MOST PREFFERED EMBODIMENTS

Figure 1B:
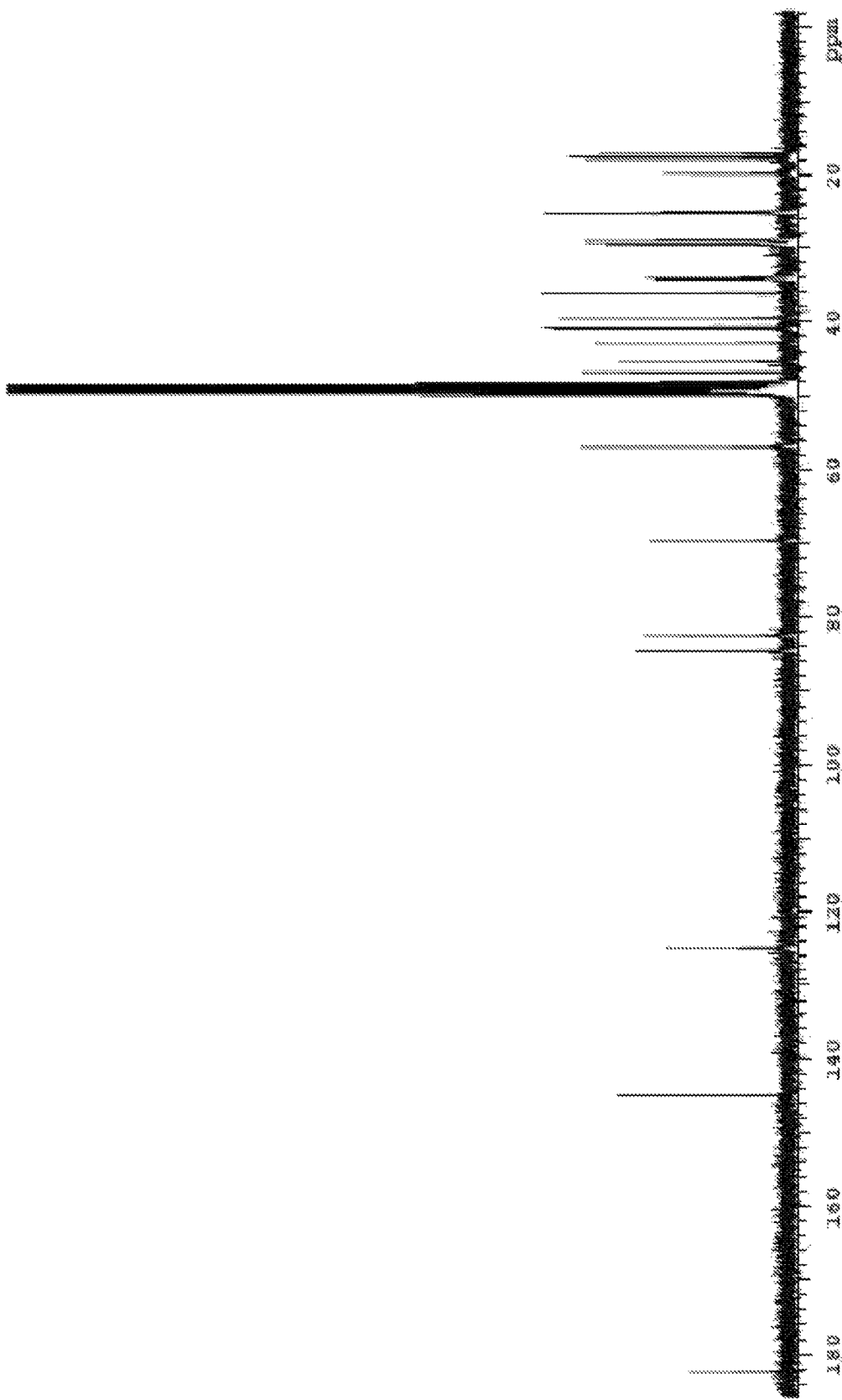
FIG. 1b shows the carbon NMR spectrum for the identification of Arjunic acid isolated from the bark of *Terminalia arjuna*.

In the most preferred embodiment, the invention discloses a novel process for the isolation of standardized composition of arjunoglucoside from bark of *Terminalia arjuna*, said process comprising steps of:

(a) Charging *Terminalia arjuna* bark powder into an extractor,
(b) Adding 3 volumes of ethanol or methanol to *Terminalia arjuna* bark powder and refluxing for 3 hours at 65 to 70° C.,
(c) Filtering the ethanol or methanol extract of step b) and concentrating under vacuum to get a brown coloured powder,
(d) Dissolving the powder obtained from step c) into 5 volumes of de-mineralize water and stirring thoroughly for 1 hr at 50-55° C. to obtain a solution,
(e) Transferring the solution from step d) to separating funnel and extracting with 2 volumes of solvent, 6 times, and separating the aqueous and organic layer,
(f) Collecting and combining the solvent fractions 1-6 from step e and concentrating under vacuum to obtain brown coloured powder,
(g) Loading the powder of step f) into a silica gel and eluting with chloroform:methanol,
(h) Identifying the compounds from step g) as Arjunic acid represented by STR#1, Arjunolic acid represented by STR#2, Arjungenin represented by STR#3, Arjunoglucoside-I represented by STR#4, Arjunoglucoside-II represented by STR#5, Arjunetin represented by STR#6, and catechin represented by STR#7.

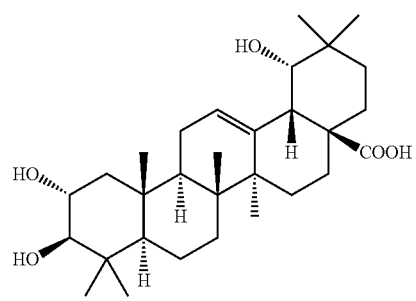

STR#1

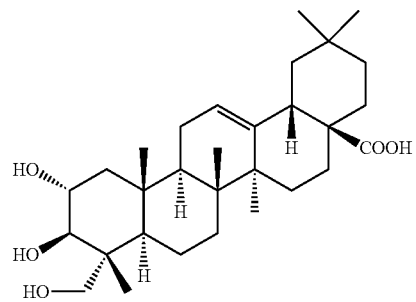

STR#2

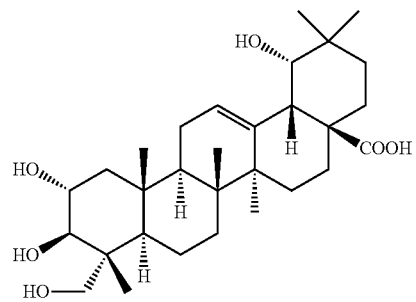

STR#3

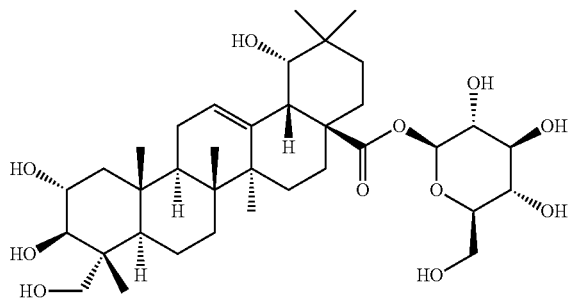

STR#4

-continued

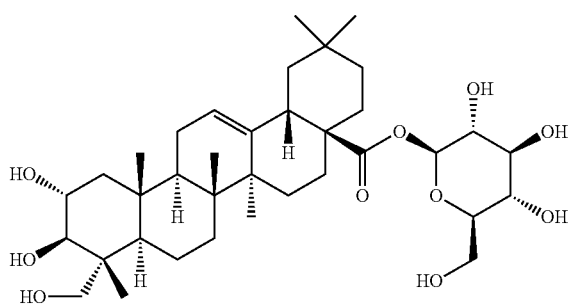
STR#5

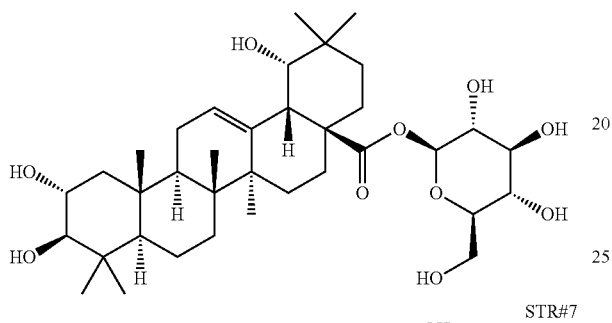
STR#6

STR#7

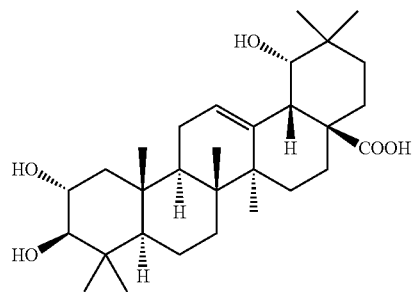

In a related embodiment, the solvent of step e) is selected from the group consisting of acetic acid, acetone, acetonitrile, benzene, carbon disulfide, carbon tetrachloride, chloroform, cyclohexane, 1,2-dichloroethane, dichloromethane, diethyl ether, 1,2-dimethoxyethane, dimethylsulfoxide, 1,4-dioxane, ethanol, ethyl acetate, hexane, isopropanol, methanol, methylethyl ketone, N,N-dimethylformamide, nitromethane, n-Propanol, pentane, pyridine, tetrahydrofuran, toluene, water or combinations thereof. In another related embodiment, the solvent of step e) is preferably ethyl acetate.

In another preferred embodiment, the invention discloses a process for enriching arjunoglucoside II, said process comprising steps of:

(a) Charging *Terminalia arjuna* bark powder into an extractor,
(b) Adding 3 volumes of ethanol or methanol to *Terminalia arjuna* bark powder and refluxing for 3 hours at 65 to 70° C.,
(c) Filtering the ethanol or methanol extract of step b) and concentrating under vacuum to get a brown coloured powder, Assay of arjunoglucoside-II by HPLC=0.55% w/w
(d) Dissolving the powder obtained from step c) into 5 volumes of de-mineralize water and stirring thoroughly for 1 hr at 50-55° C. to obtain a solution,
(e) Transferring the solution from step d) to separating funnel and extracting with 2 volumes of solvent, 6 times, and separating the aqueous and organic layer,
(f) Collecting and combining the solvent fractions 1-6 from step e and concentrating under vacuum to obtain brown coloured powder, Assay of arjunoglucoside-II by HPLC=20-21% w/w.

In another preferred embodiment, the invention discloses a composition comprising atleast 3% arjunoglucosides wherein said composition comprises Arjunic acid represented by STR#1, Arjunolic acid represented by STR#2, Arjungenin represented by STR#3, Arjunoglucoside-I represented by STR#4, Arjunoglucoside-II represented by STR#5, Arjunetin represented by STR#6, and catechin represented by STR#7.

STR#1

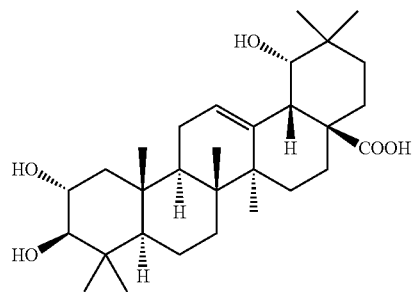

STR#2

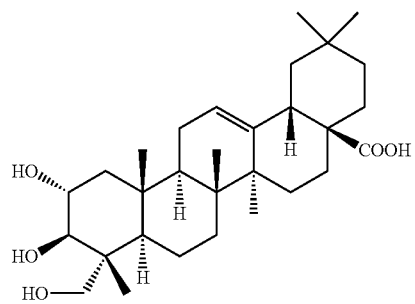

STR#3

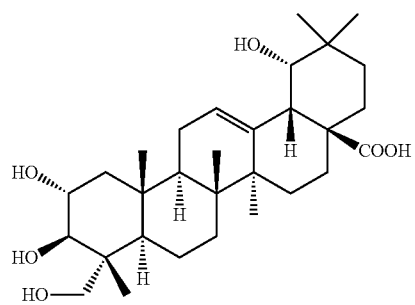

STR#4

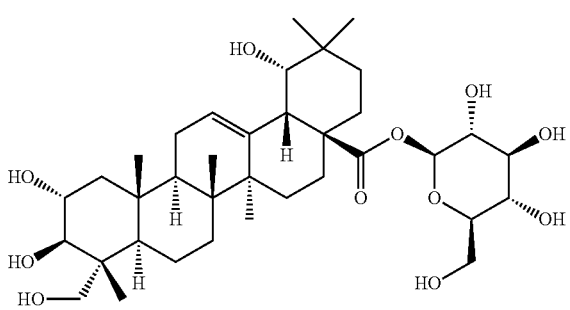

-continued

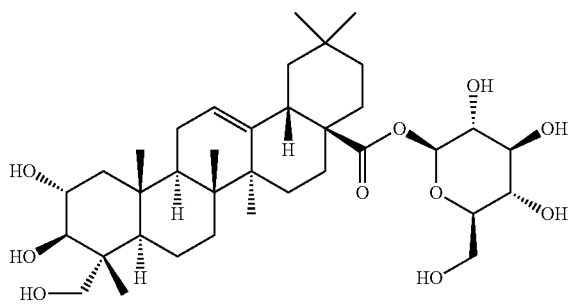

STR#5

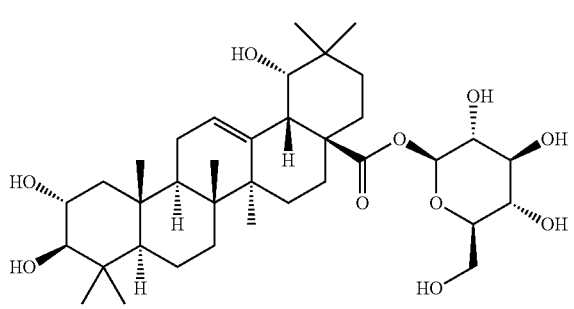

STR#6

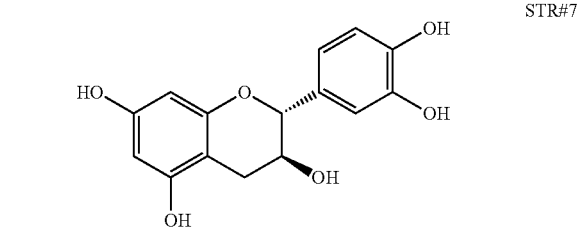

STR#7

The specific examples included herein below illustrate the aforesaid most preferred embodiments of the present invention.

EXAMPLE 1

Process for Isolating Arjunoglucosides from the Bark of *Terminalia arjuna*

Figure 2A:
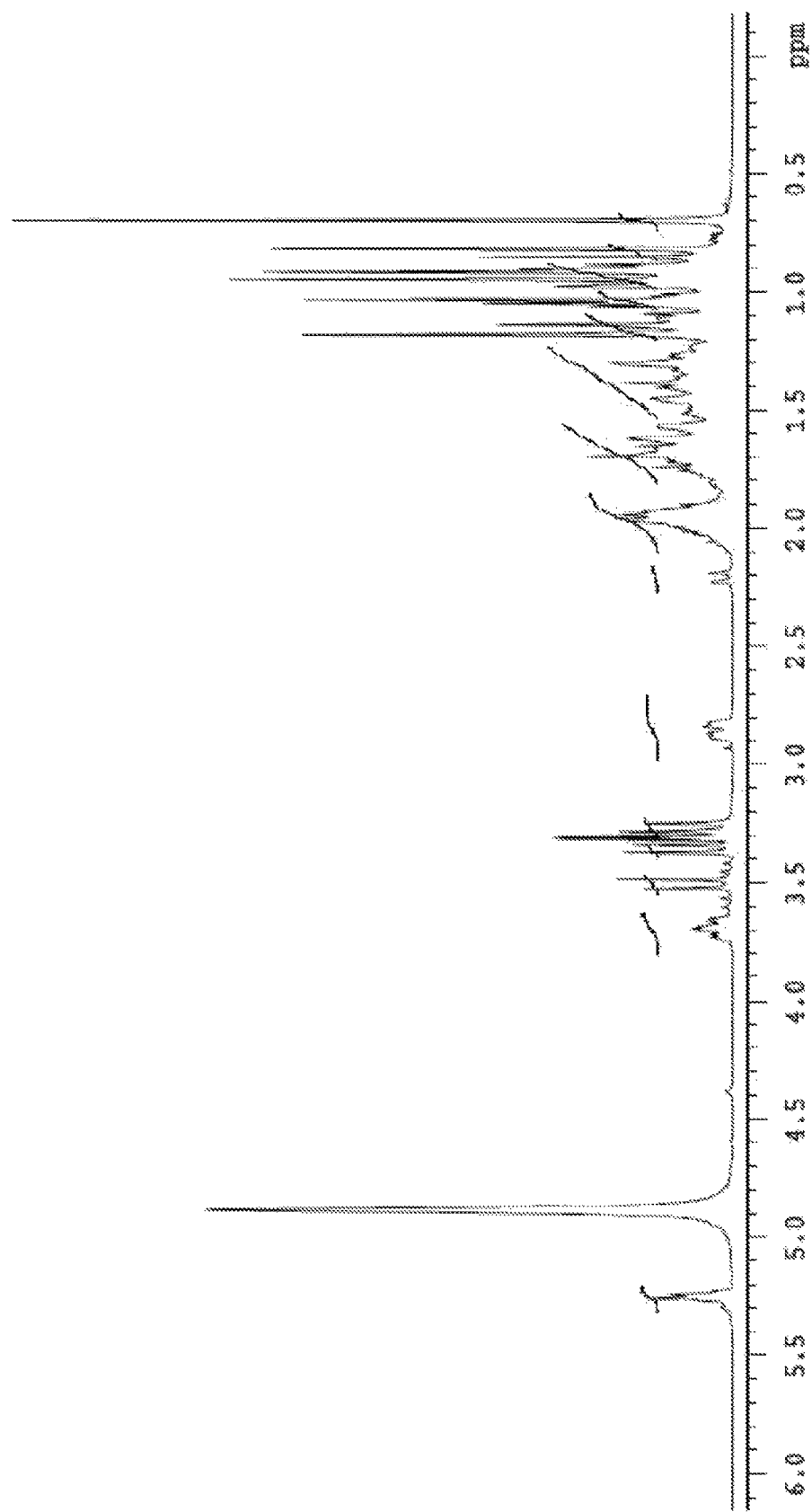
FIG. 2a shows the proton NMR spectrum for the identification of Arjunolic acid isolated from the bark of *Terminalia arjuna*.
Figure 2B:
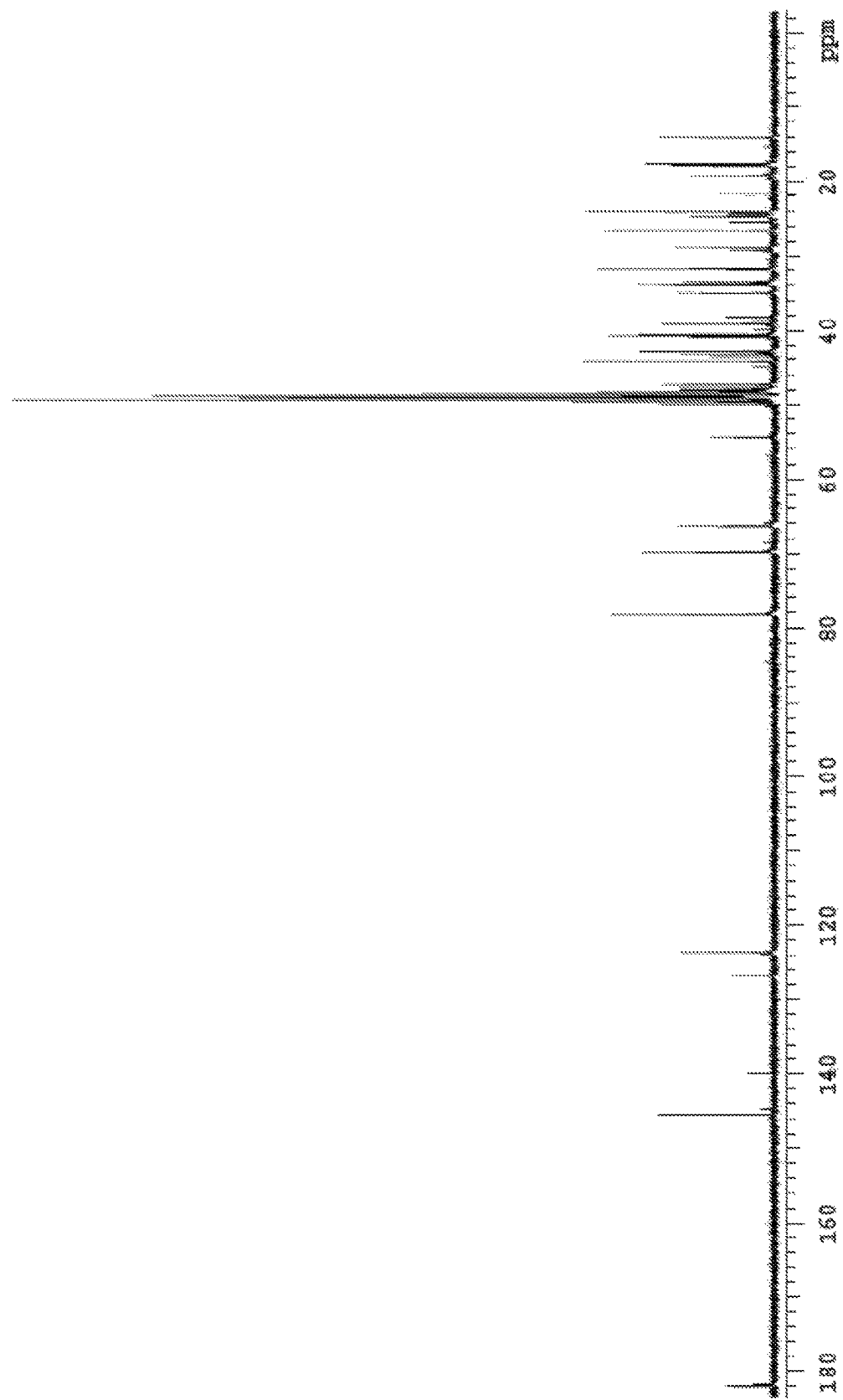
FIG. 2b shows the carbon NMR spectrum for the identification of Arjunolic acid, isolated from the bark of *Terminalia arjuna*.
Figure 3A:
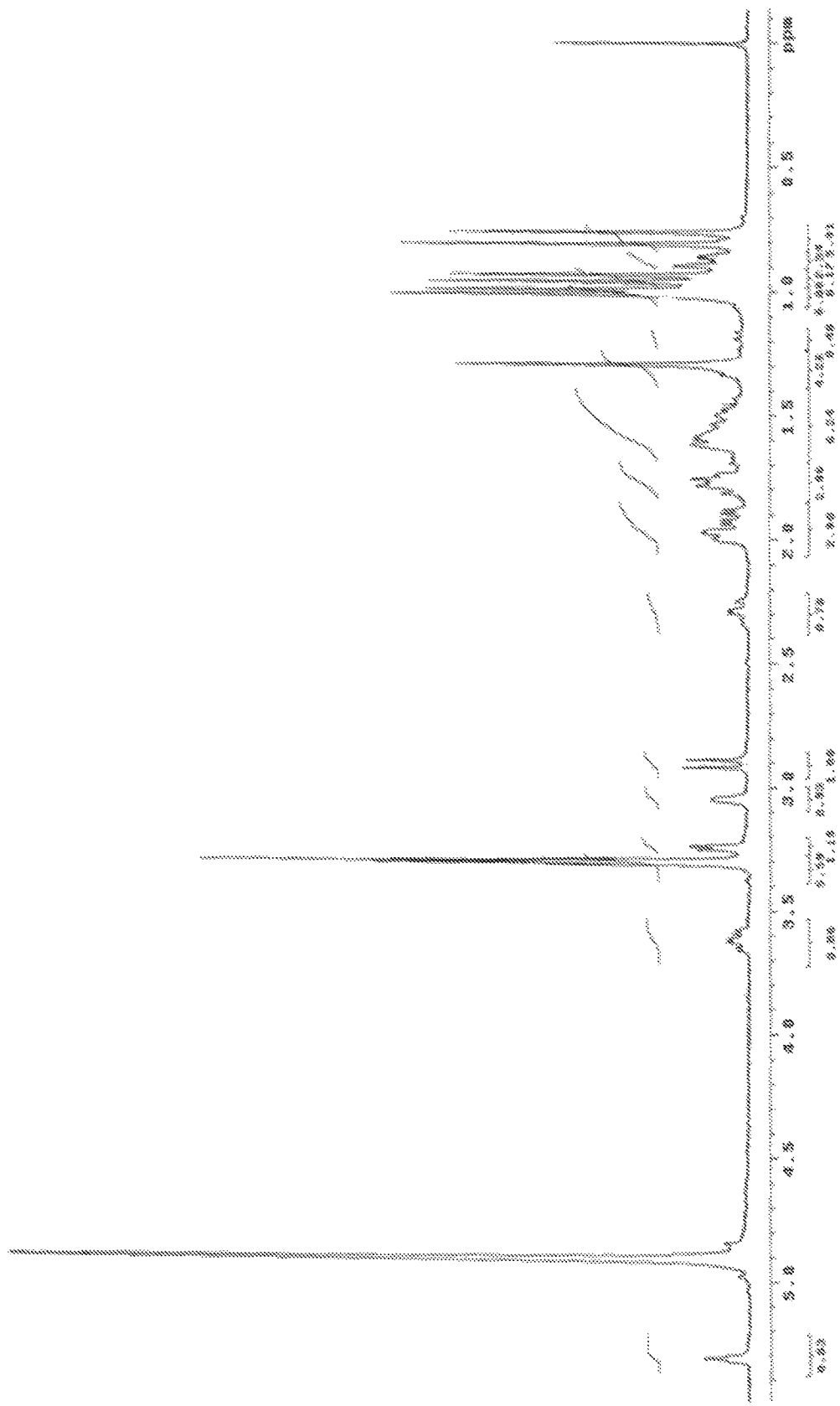
FIG. 3a shows the proton NMR spectrum for the identification of Arjungenin isolated from the bark of *Terminalia arjuna*.
Figure 3B:
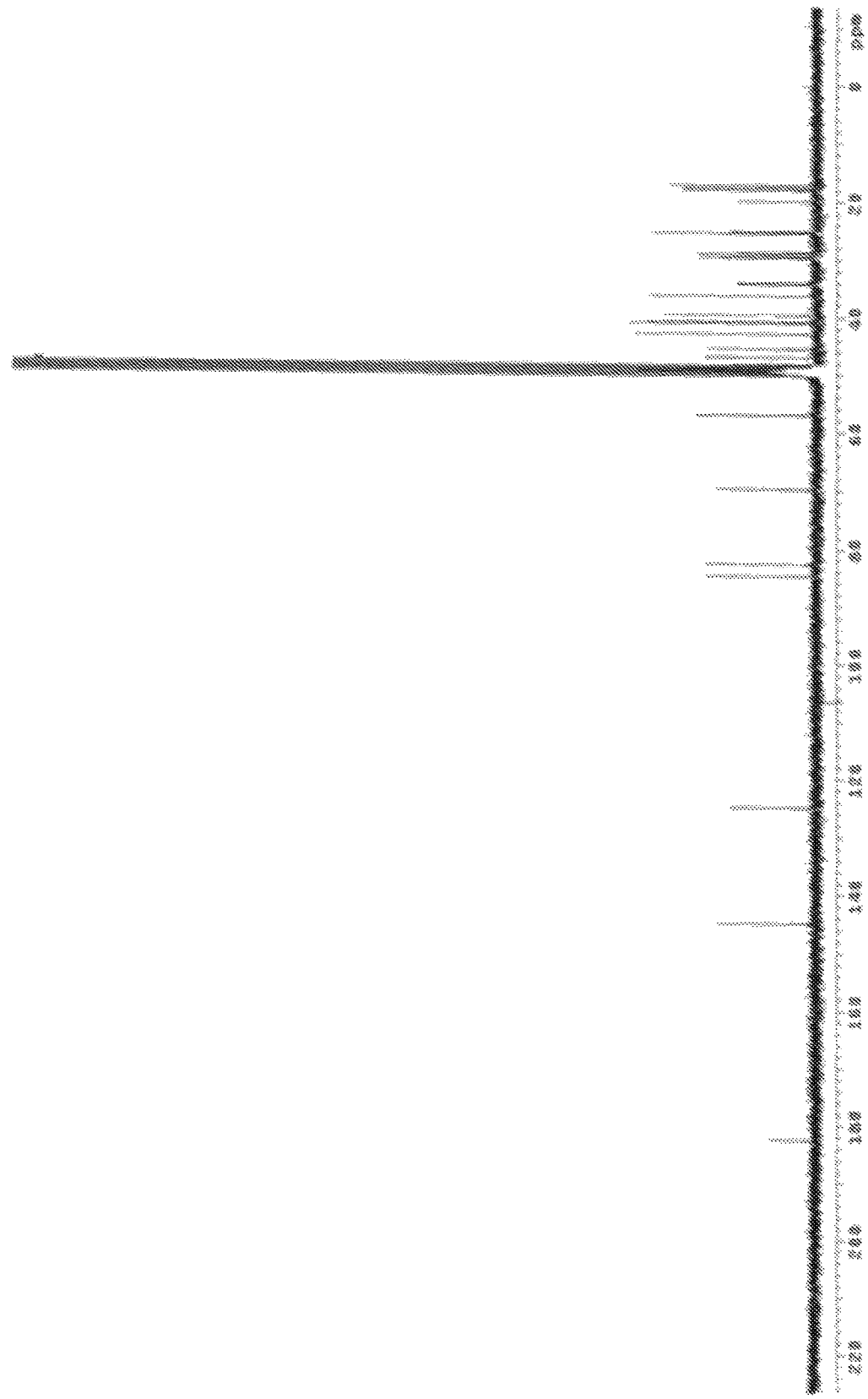
FIG. 3b shows the carbon NMR spectrum for the identification of Arjungenin isolated from the bark of *Terminalia arjuna*.
Figure 4A:
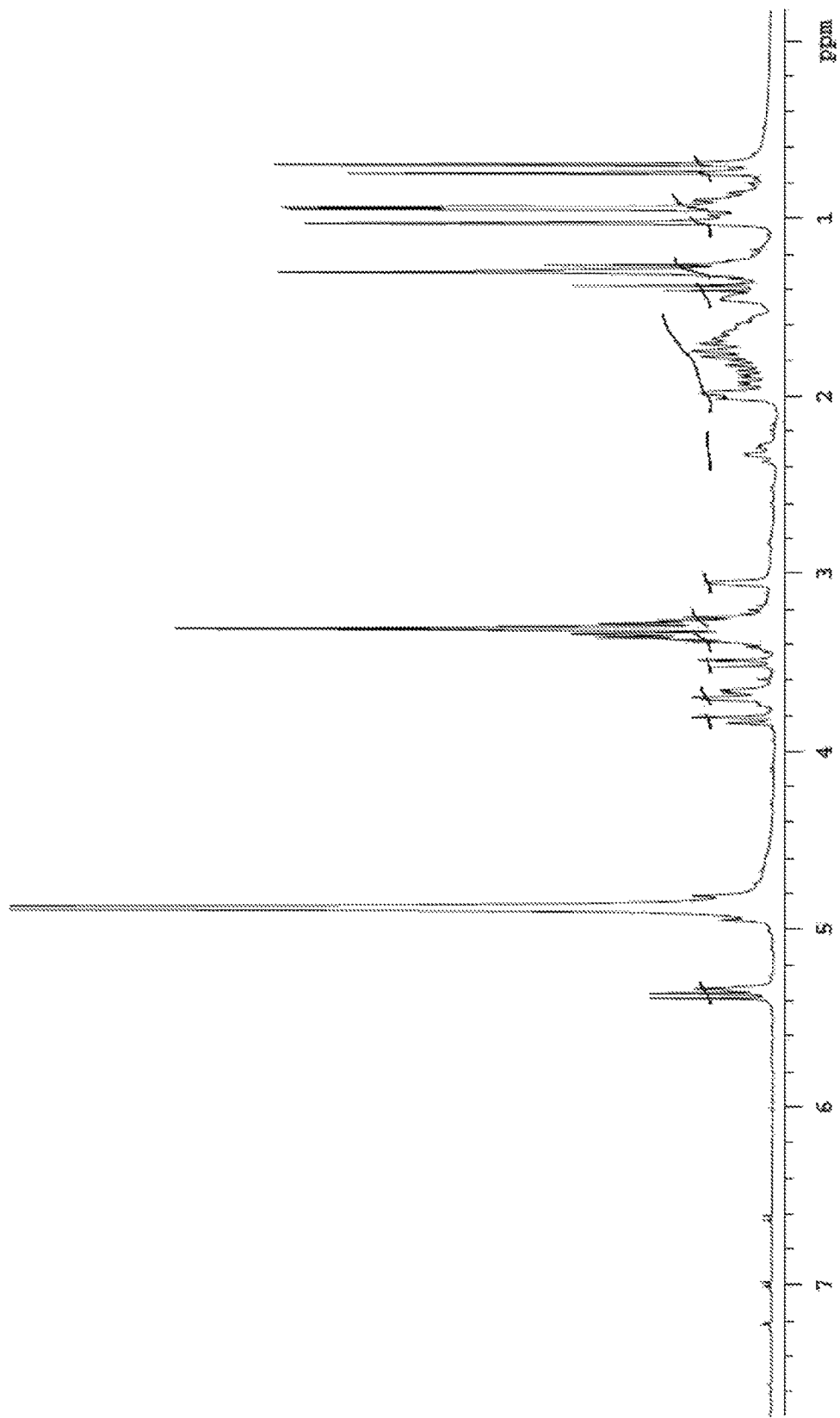
FIG. 4a shows the proton NMR spectrum for the identification of Arjunoglucoside-I isolated from the bark of *Terminalia arjuna*.
Figure 5A:
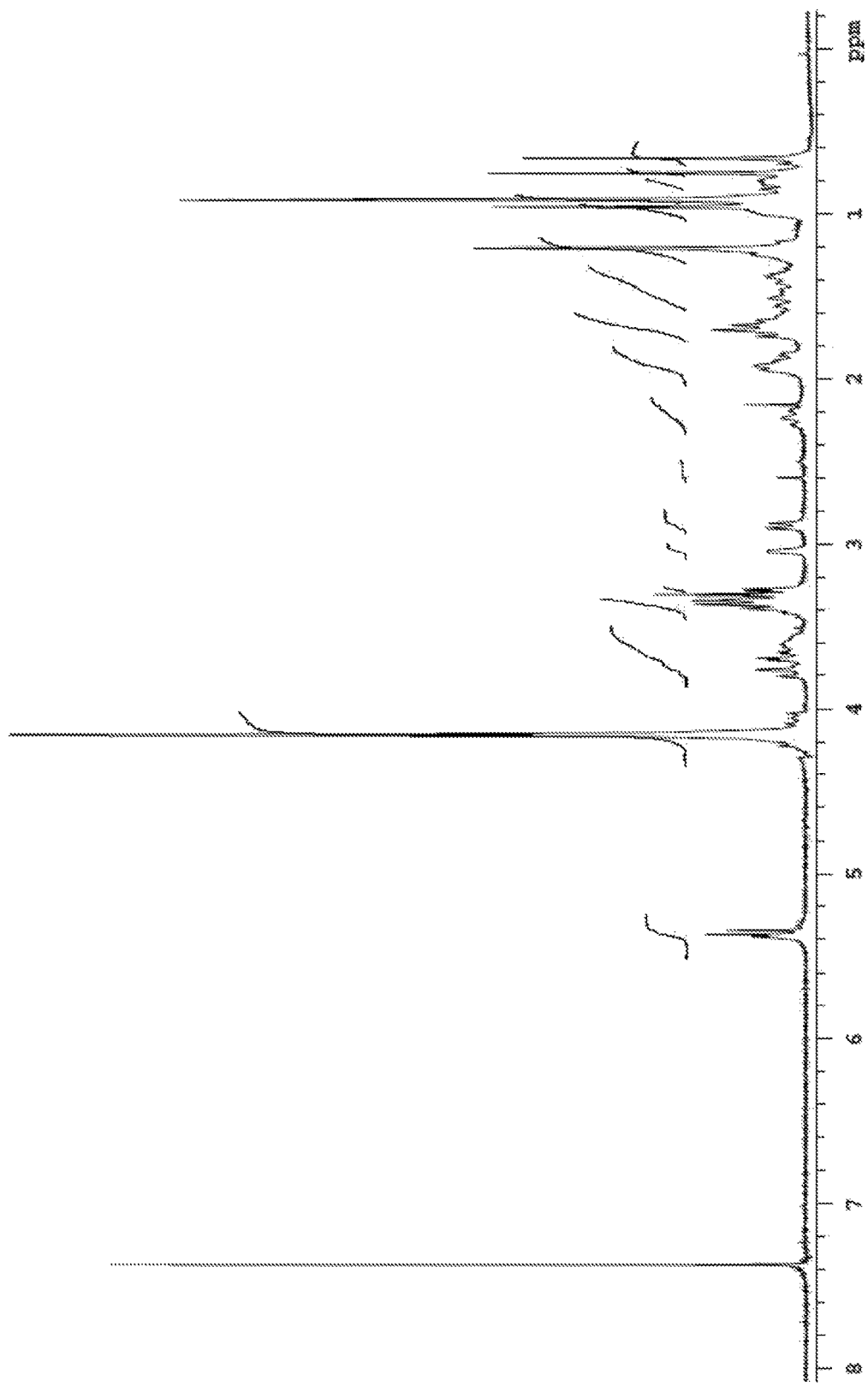
FIG. 5a shows the proton NMR spectrum for the identification of Arjunoglucoside-II isolated from the bark of *Terminalia arjuna*.
Figure 5B:
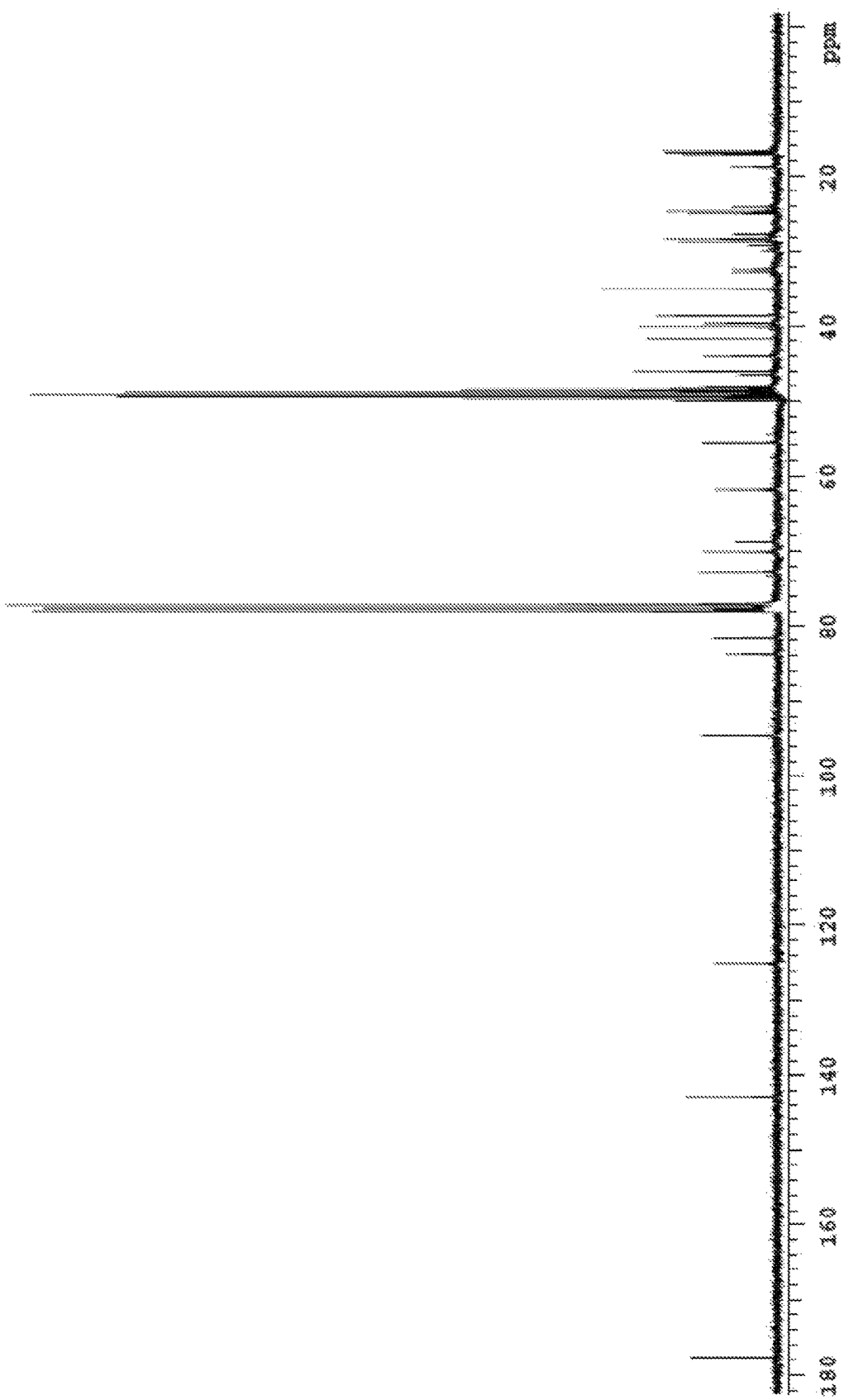
FIG. 5b shows the carbon NMR spectrum for the identification of Arjunoglucoside-II isolated from the bark of *Terminalia arjuna*.
Figure 6B:
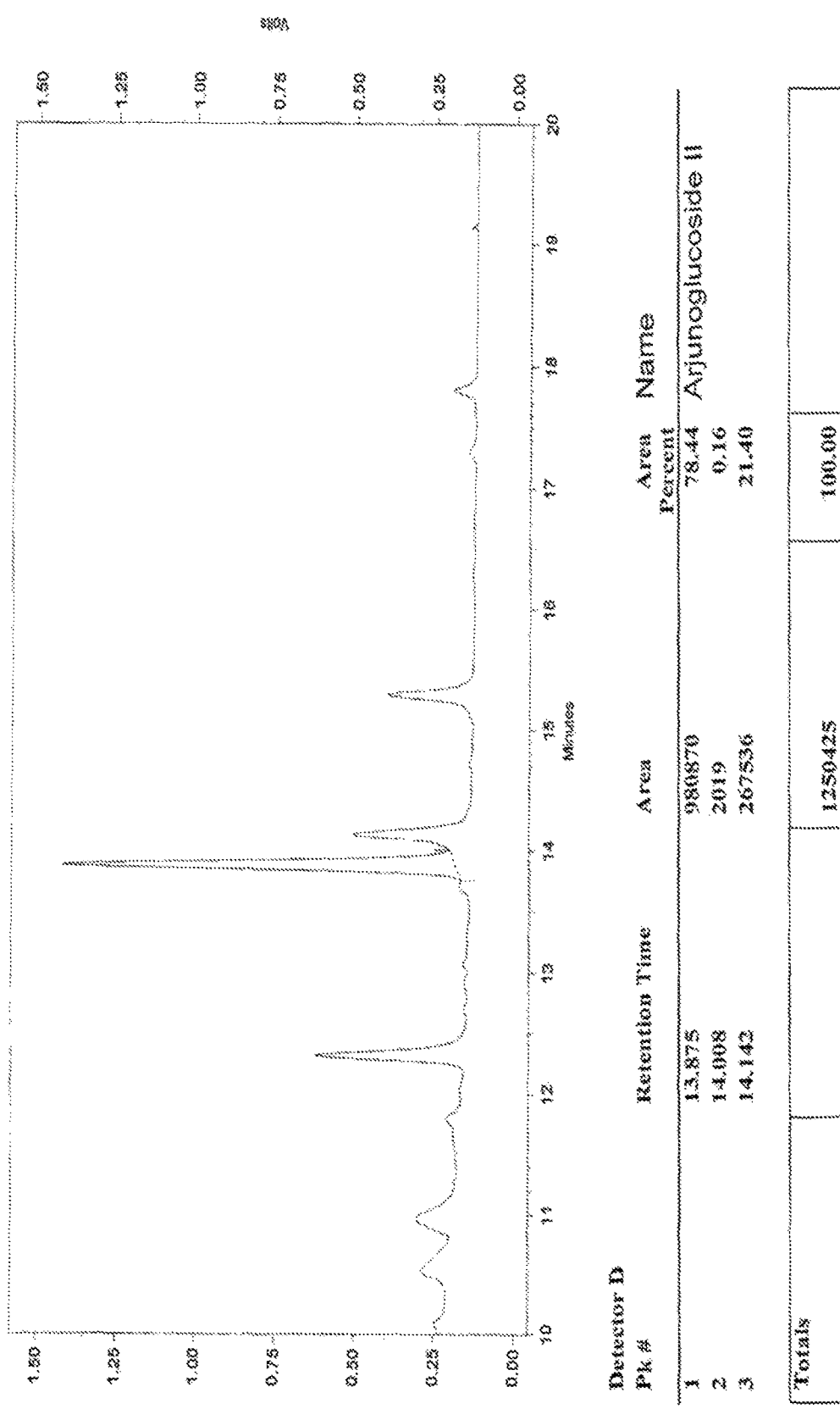
FIG. 6b shows the HPLC chromotogram for the identification of enriched Arjunoglucoside-II isolated from the bark of *Terminalia arjuna*.
Figure 7A:
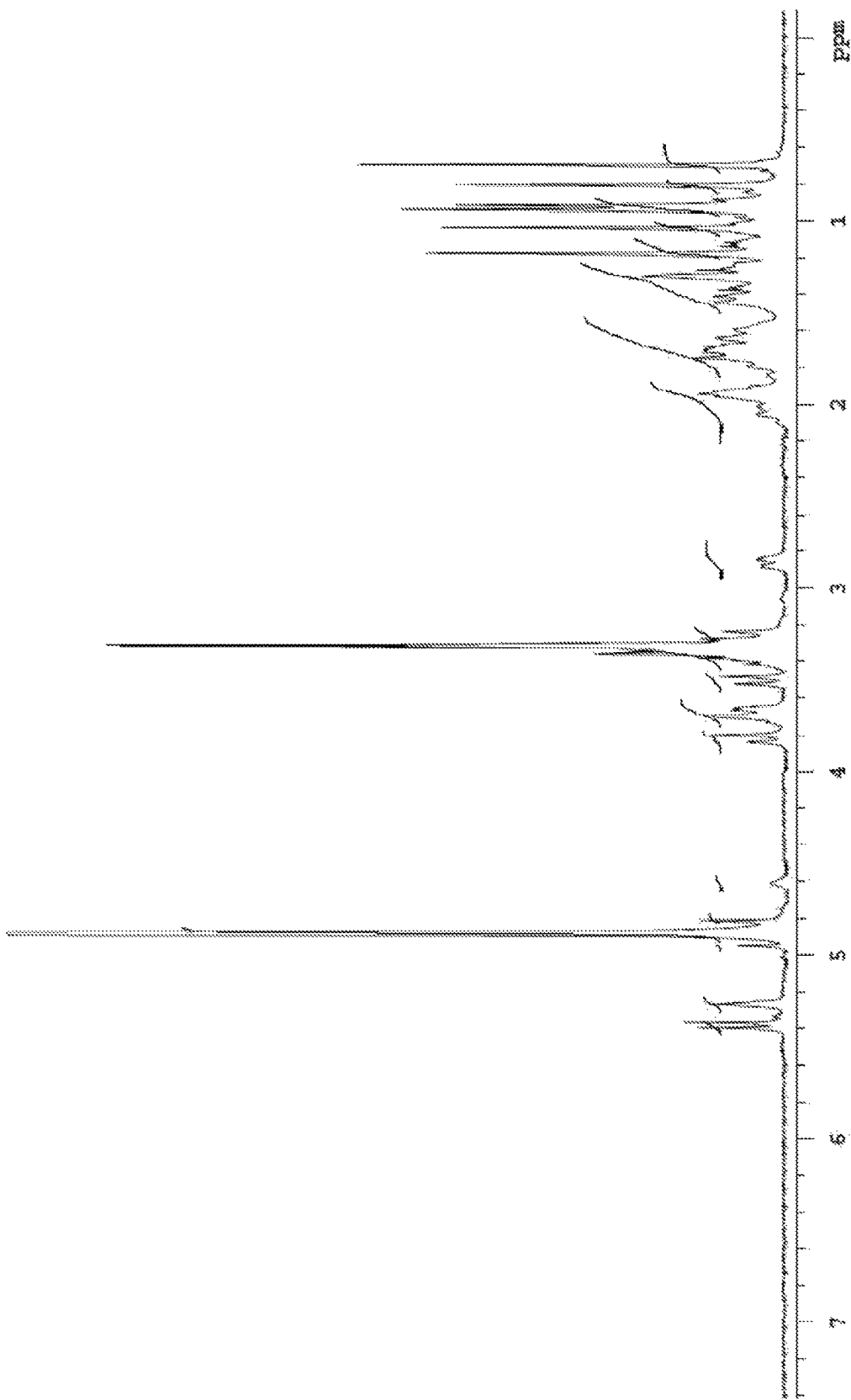
FIG. 7a shows the proton NMR spectrum for the identification of Arjunetin isolated from the bark of *Terminalia arjuna*.
Figure 7B:
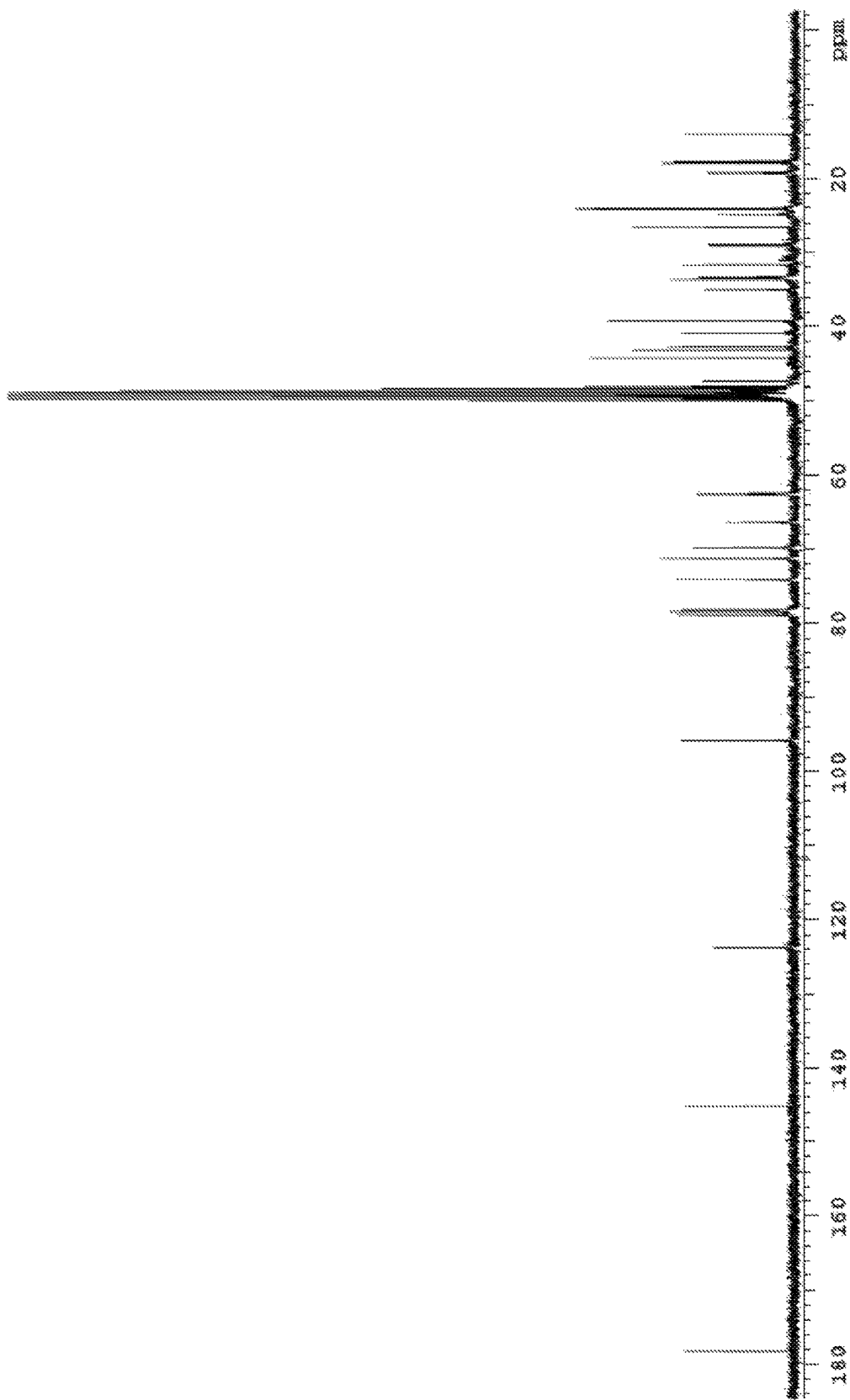
FIG. 7b shows the carbon NMR spectrum for the identification of Arjunetin isolated from the bark of *Terminalia arjuna*.
Figure 8A:
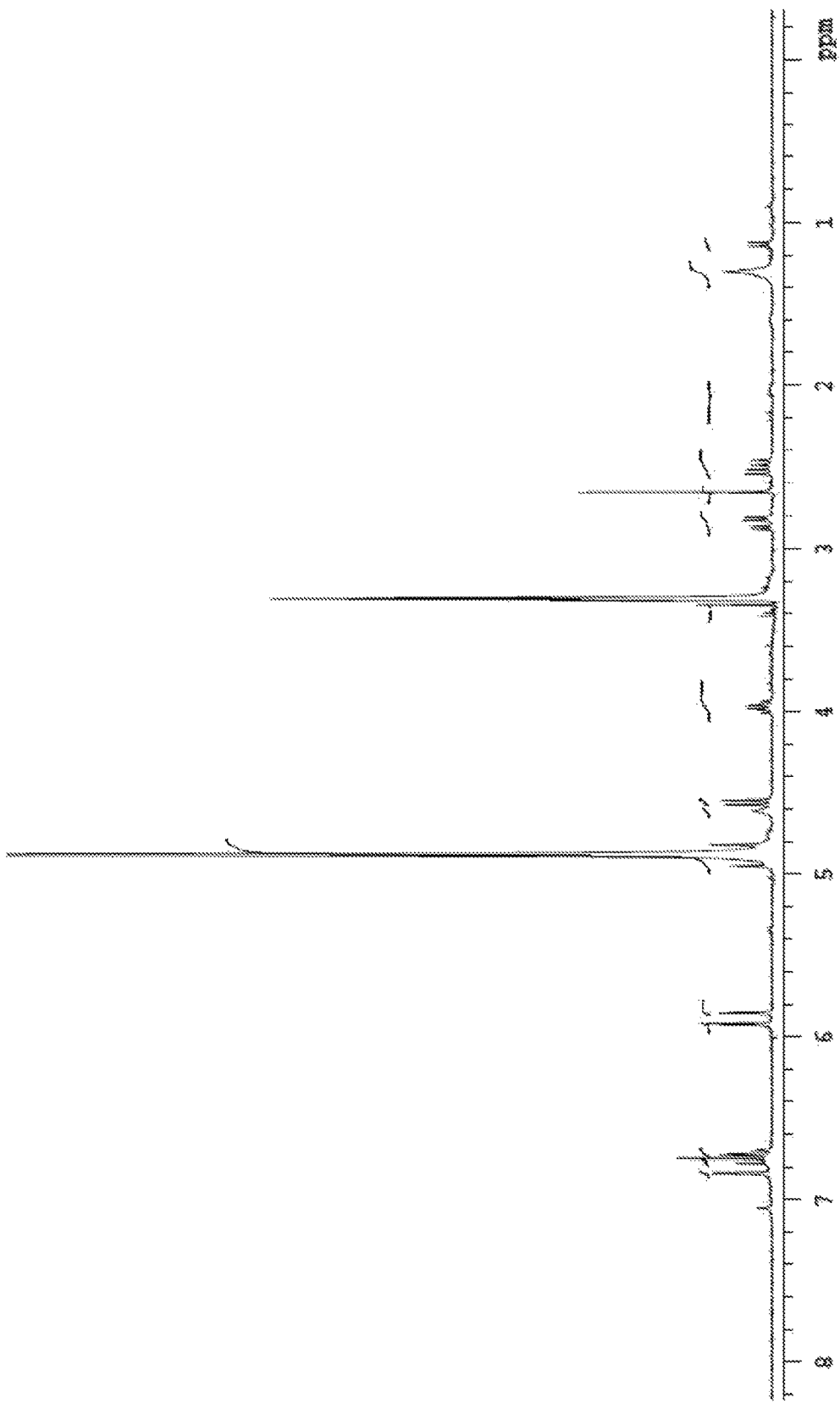
FIG. 8a shows the proton NMR spectrum for the identification of catechin isolated from the bark of *Terminalia arjuna*.
Figure 8B:
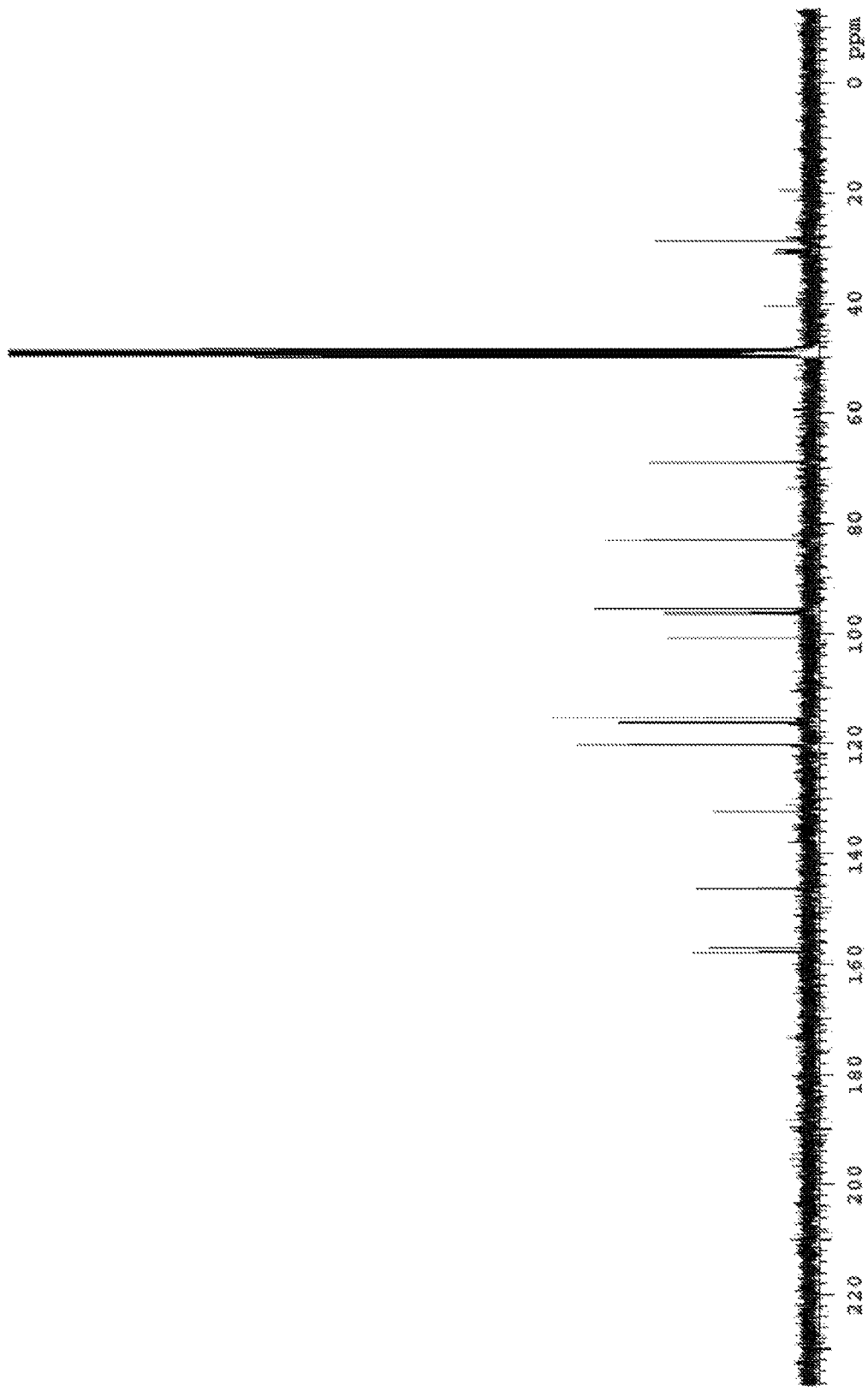
FIG. 8b shows the carbon NMR spectrum for the identification of catechin isolated from the bark of *Terminalia arjuna*.

The present invention discloses a process for isolating arjunoglucosides from *Terminalia arjuna*. The process contains the following step of charging 2 kg of *Terminalia arjuna* bark powder into an extractor. Then added 3 volumes of methanol to *Terminalia arjuna* bark powder and refluxed for 3 hours at 65 to 70° C. The solution was then filtered and concentrated under vacuum to get a brown coloured powder, Assay of arjunoglucoside-II by HPLC=0.55% w/w, Yield approx. 500 g (25%). The powder was then dissolved into 5 volumes of de-mineralize water and stirred thoroughly for 1 hr at 50-55° C. The solution was then transferred to separating funnel and extracted with 2 volumes of ethyl acetate, 6 times, and the aqueous and organic layers were separated. The 6 ethyl acetate fractions were collected and concentrated under vacuum to obtain brown coloured powder, assay of arjunoglucoside-II by HPLC=20-21% w/w, yield approx. 40 g. The powder was then loaded into a silica gel and eluted with chloroform:methanol. This fraction contains Arjunic acid, Arjunolic acid, Arjungenin, Arjunoglucoside-I & II, Arjunetin and catechin. The compounds were then identified using NMR as Arjunic acid (FIGS. 1a and 1b), Arjunolic acid (FIGS. 2a and 2b), Arjungenin (FIGS. 3a and 3b), Arjunoglucoside-I (FIGS. 4a and 4b), Arjunoglucoside-II (FIGS. 5a, 5b, 6a and 6b), Arjunetin (FIGS. 7a and 7b), and catechin (FIGS. 8a and 8b).

A composition containing atleast 3% arjunoglucosides comprising Arjunic acid, Arjunolic acid, Arjungenin, Arjunoglucoside-I, Arjunoglucoside-II, Arjunetin, and catechin was also formulated.

While the invention has been described with reference to a preferred embodiment, it is to be clearly understood by those skilled in the art that the invention is not limited thereto. Rather, the scope of the invention is to be interpreted only in conjunction with the appended claims.

We claim:

1. A process for the isolation of standardized composition comprising of arjunoglucoside from bark of *Terminalia arjuna*, said process comprising steps of:
    (a) Charging *Terminalia arjuna* bark powder into an extractor,
    (b) Adding 3 volumes of ethanol or methanol to *Terminalia arjuna* bark powder and refluxing for 3 hours at 65 to 70° C.,
    (c) Filtering the ethanol or methanol extract of step b) and concentrating under vacuum to get a brown coloured powder,
    (d) Dissolving the powder obtained from step c) into 5 volumes of de-mineralize water and stirring thoroughly for 1 hr at 50-55° C. to obtain a solution,
    (e) Transferring the solution from step d) to separating funnel and extracting with 2 volumes of ethyl acetate, 6 times, and separating the aqueous and organic layer,
    (f) Collecting and combining the ethyl acetate fractions 1-6 from step e and concentrating under vacuum to obtain brown coloured powder,
    (g) Loading the powder of step 1) into a silica gel and eluting with chloroform:methanol,
    (h) Identifying the compounds from step g) as Arjunic acid corresponding to STR#1, Arjunolic acid corresponding to STR#2, Arjungenin corresponding to STR#3, Arjunoglucoside-I corresponding to STR#4, Arjunoglucoside-II corresponding to STR#5, Arjunetin corresponding to STR#6, and catechin corresponding to STR#7

STR#1

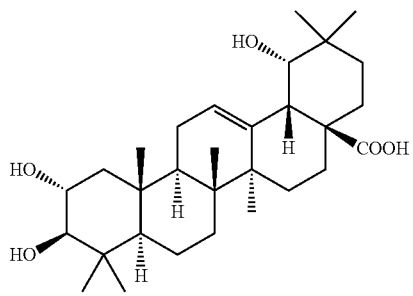

STR#2

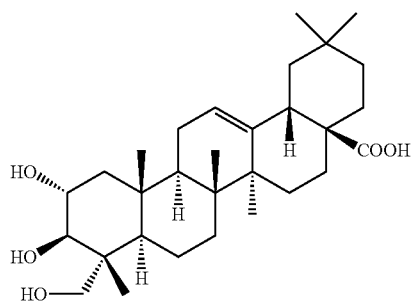

STR#3

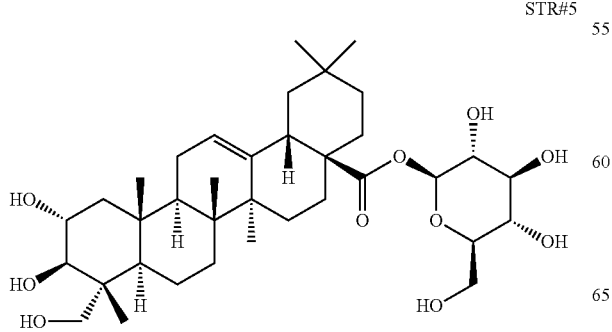

STR#4

STR#5

STR#6

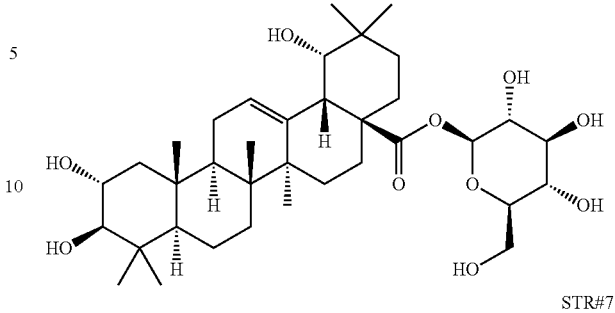

STR#7

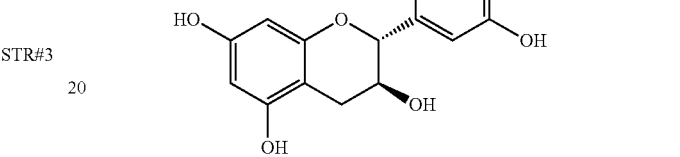

2. A process for enriching arjunoglucoside II, said process comprising steps of:
(a) Charging *Terminalia arjuna* bark powder into an extractor,
(b) Adding 3 volumes of ethanol or methanol to *Terminalia arjuna* bark powder and refluxing for 3 hours at 65 to 70° C.,
(c) Filtering the ethanol or methanol extract of step b) and concentrating under vacuum to get a brown coloured powder, Assay of arjunoglucoside-II by HPLC=0.55% w/w
(d) Dissolving the powder obtained from step c) into 5 volumes of de-mineralize water and stirring thoroughly for 1 hr at 50-55° C. to obtain a solution,
(e) Transferring the solution from step d) to separating funnel and extracting with 2 volumes of ethyl acetate, 6 times, and separating the aqueous and organic layer,
(f) Collecting and combining the ethyl acetate fractions 1-6 from step e and concentrating under vacuum to obtain brown coloured powder, Assay of arjunoglucoside-II by HPLC=20-21% w/w.

3. A composition comprising at-least 3% arjunoglucosides wherein said composition comprises Arjunic acid corresponding to STR#1, Arjunolic acid corresponding to STR#2, Arjungenin corresponding to STR#3, Arjunoglucoside-I corresponding to STR#4, Arjunoglucoside-I corresponding to STR#5, Arjunetin corresponding to STR#6, and catechin corresponding to STR#7

STR#1

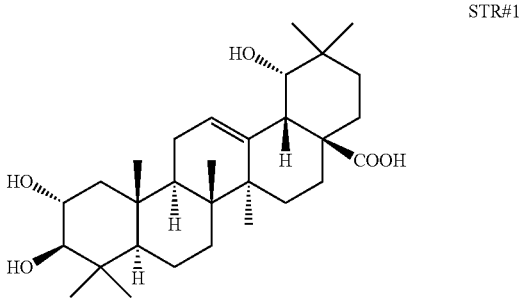

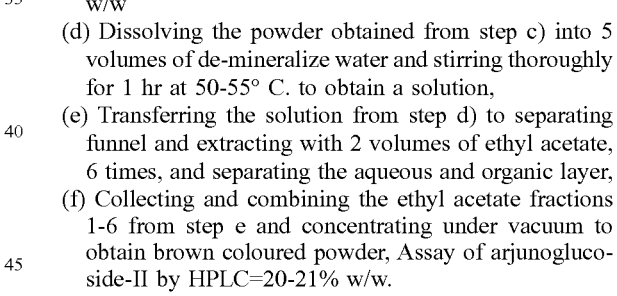

-continued
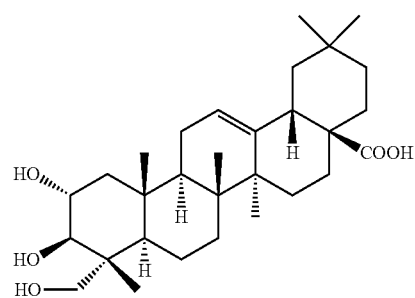
STR#2
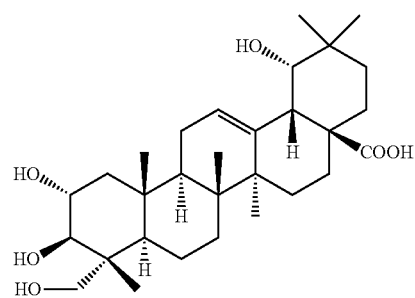
STR#3
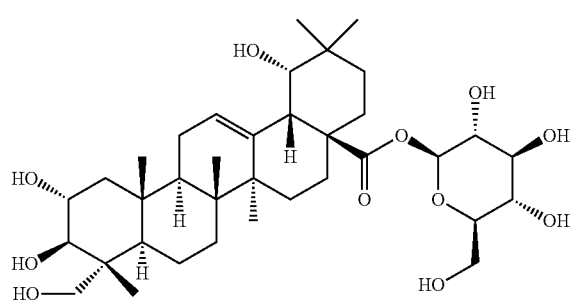
STR#4
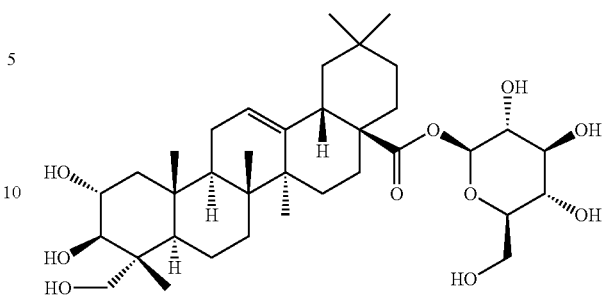
STR#5
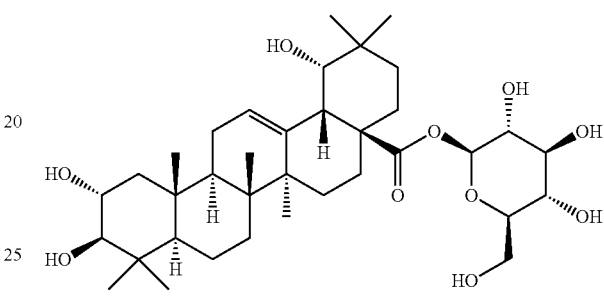
STR#6
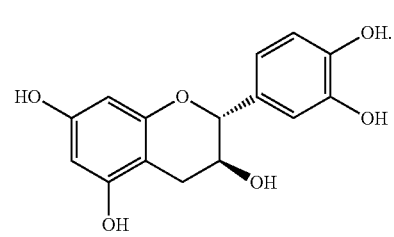
STR#7
* * * * *